US007545914B2

(12) United States Patent
Kito et al.

(10) Patent No.: US 7,545,914 B2
(45) Date of Patent: Jun. 9, 2009

(54) RADIATION IMAGE CAPTURING SYSTEM

(75) Inventors: Eiichi Kito, Minami-ashigara (JP);
Naoyuki Nishino, Minami-ashigara (JP);
Yasunori Ohta, Yokohama (JP);
Tsuyoshi Tanabe, Odawara (JP);
Takuya Yoshimi, Yokohama (JP);
Takeshi Kuwabara, Minami-ashigara (JP); Kazuharu Ueta, Suginami-ku (JP);
Makoto Iriuchijima, Ora-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 12/179,740

(22) Filed: Jul. 25, 2008

(65) Prior Publication Data

US 2009/0026391 A1 Jan. 29, 2009

(30) Foreign Application Priority Data

Jul. 27, 2007 (JP) ............................. 2007-195935
Feb. 26, 2008 (JP) ............................. 2008-044366
Jun. 9, 2008 (JP) ............................. 2008-150345

(51) Int. Cl.
*H05G 1/64* (2006.01)
*H05G 1/70* (2006.01)
*G01D 18/00* (2006.01)

(52) U.S. Cl. ..................... 378/98.8; 378/91; 378/207

(58) Field of Classification Search ............... 378/98.8, 378/91, 207, 116, 189, 190, 162, 165
See application file for complete search history.

(56) References Cited

U.S. PATENT DOCUMENTS 7,046,764 B1 * 5/2006 Kump ...................... 378/117
7,127,032 B1 * 10/2006 Kump ...................... 378/117

FOREIGN PATENT DOCUMENTS

JP 2007-037837 A 2/2007

* cited by examiner

*Primary Examiner*—Irakli Kiknadze
(74) *Attorney, Agent, or Firm*—Sughrue Mion, PLLC

(57) ABSTRACT

A radiation image capturing system detects the position of a radiation detecting cassette disposed below a patient and the position of a radiation source for emitting a radiation, based on the differences between the propagation times of radio waves emitted from an antenna device to an image capturing apparatus and the radiation detecting cassette. Based on the detected positions, the relative positions of the image capturing apparatus and the radiation detecting cassette are calculated, and then compared with each other by a position determining unit to judge how the image capturing apparatus is positioned with respect to the radiation detecting cassette. If the image capturing apparatus is not positioned in head-on facing relation to the radiation detecting cassette, then a warning is issued, and an actuating mechanism moves the image capturing apparatus to an appropriate position.

6 Claims, 13 Drawing Sheets

RADIATION IMAGE CAPTURING SYSTEM

BACKGROUND OF THE INVENTION

1. Field of the Invention

The present invention relates to a radiation image capturing system having a radiation conversion panel for converting a radiation that has passed through a subject into radiation image information.

2. Description of the Related Art

In the medical field, there have widely been used radiation image capturing apparatus which apply a radiation to a subject and guide the radiation that has passed through the subject to a radiation conversion panel, which captures a radiation image from the radiation. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor. In such a radiation conversion panel, the radiation film with the recorded radiation image is supplied to a developing device to develop the image, or the stimulable phosphor panel is supplied to a reading device to obtain the radiation image as a visible image.

In the operating room or the like, it is necessary to read out and display a recorded radiation image immediately from a radiation conversion panel after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read out a detected radiation image.

Such a radiation image capturing system is disclosed in Japanese Laid-Open Patent Publication No. 2007-037837, for example. In the disclosed radiation image capturing system, a radiation source for radiating X-rays is disposed above a subject lying on a lying table, and an X-ray image receiver is disposed below an affected part of the subject. X-rays emitted from the radiation source pass through the affected part of the subject, and detected by the X-ray image receiver, which converts the X-rays into an electric image signal.

In the radiation image capturing system, the X-ray image receiver has an image capturing surface which needs to be disposed in facing relation to the radiation source and the subject that are positioned upwardly of the X-ray image receiver. However, when the X-ray image receiver is positioned in alignment with the affected part of the subject, the X-ray image receiver may not be properly positioned in head-on alignment with the radiation source. If an image capturing cycle is carried out while the X-ray image receiver is not facing the radiation source head-on, then the X-ray image receiver is unable to capture a radiation image of the affected part of the subject. Therefore, it is necessary to reset the X-ray image receiver in a desired position and then to perform an image capturing cycle. As a result, the efficiency of the process of capturing a radiation image of the affected part of the subject is relatively low.

SUMMARY OF THE INVENTION

It is a general object of the present invention to provide a radiation image capturing system which allows a radiation conversion panel to be reliably and accurately placed in a desired position that faces a radiation source head-on, for thereby efficiently capturing a radiation image of a subject.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
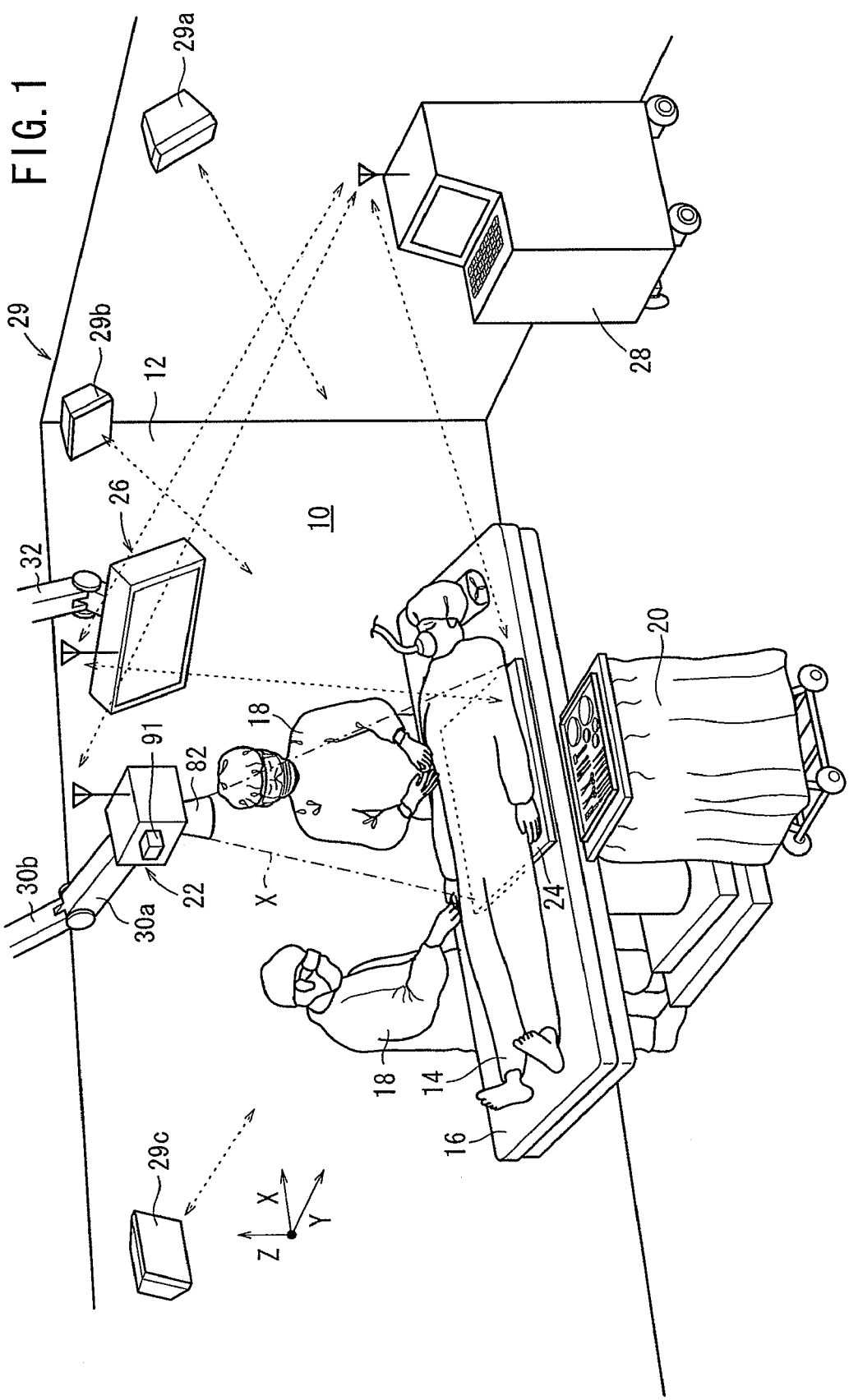
FIG. 1 is a perspective view inside an operating room incorporating a radiation image capturing system according to an embodiment of the present invention.
Figure 2:
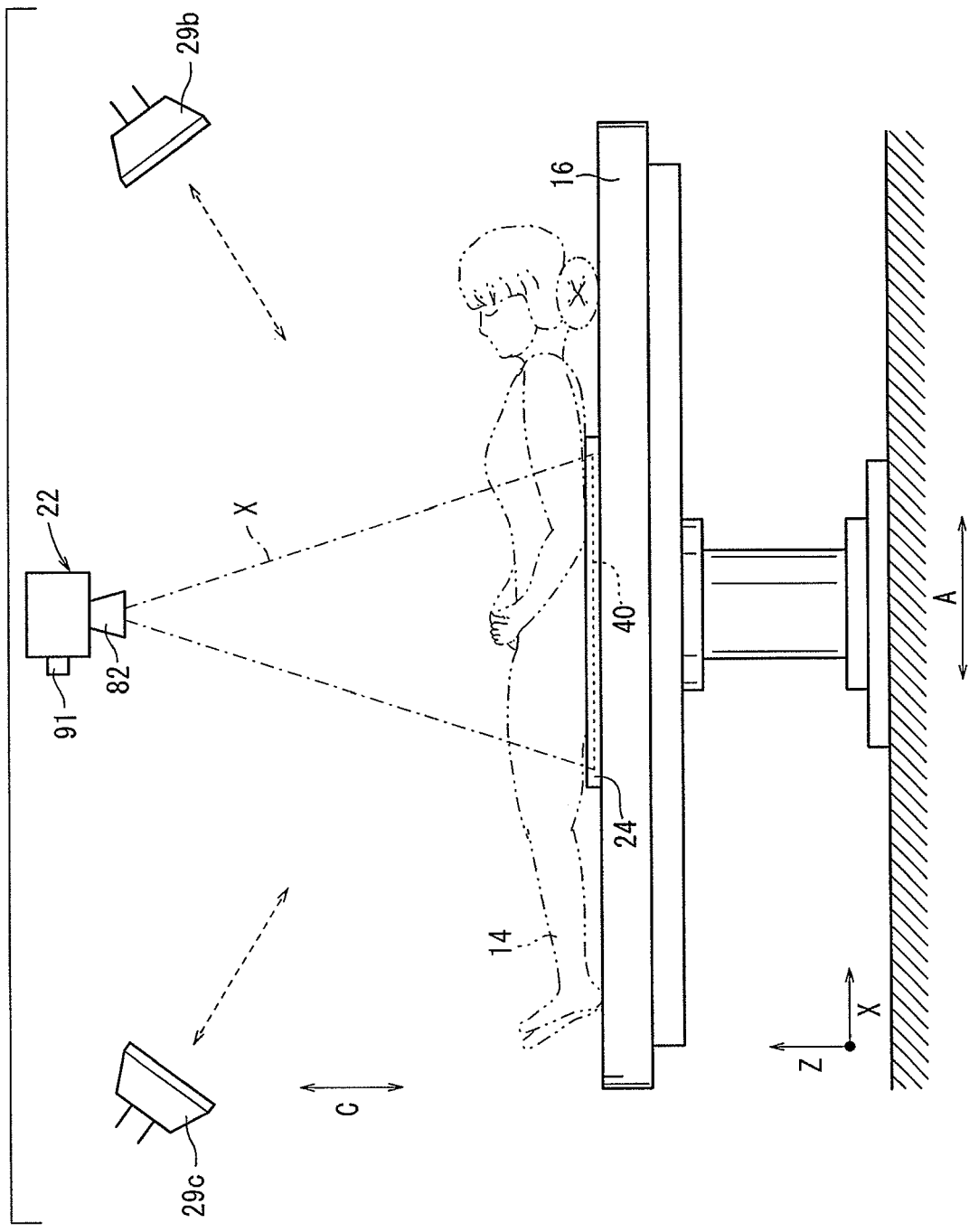
FIG. 2 is a side elevational view of a surgical table with a patient lying thereon in the operating room shown in FIG. 1.
Figure 3:
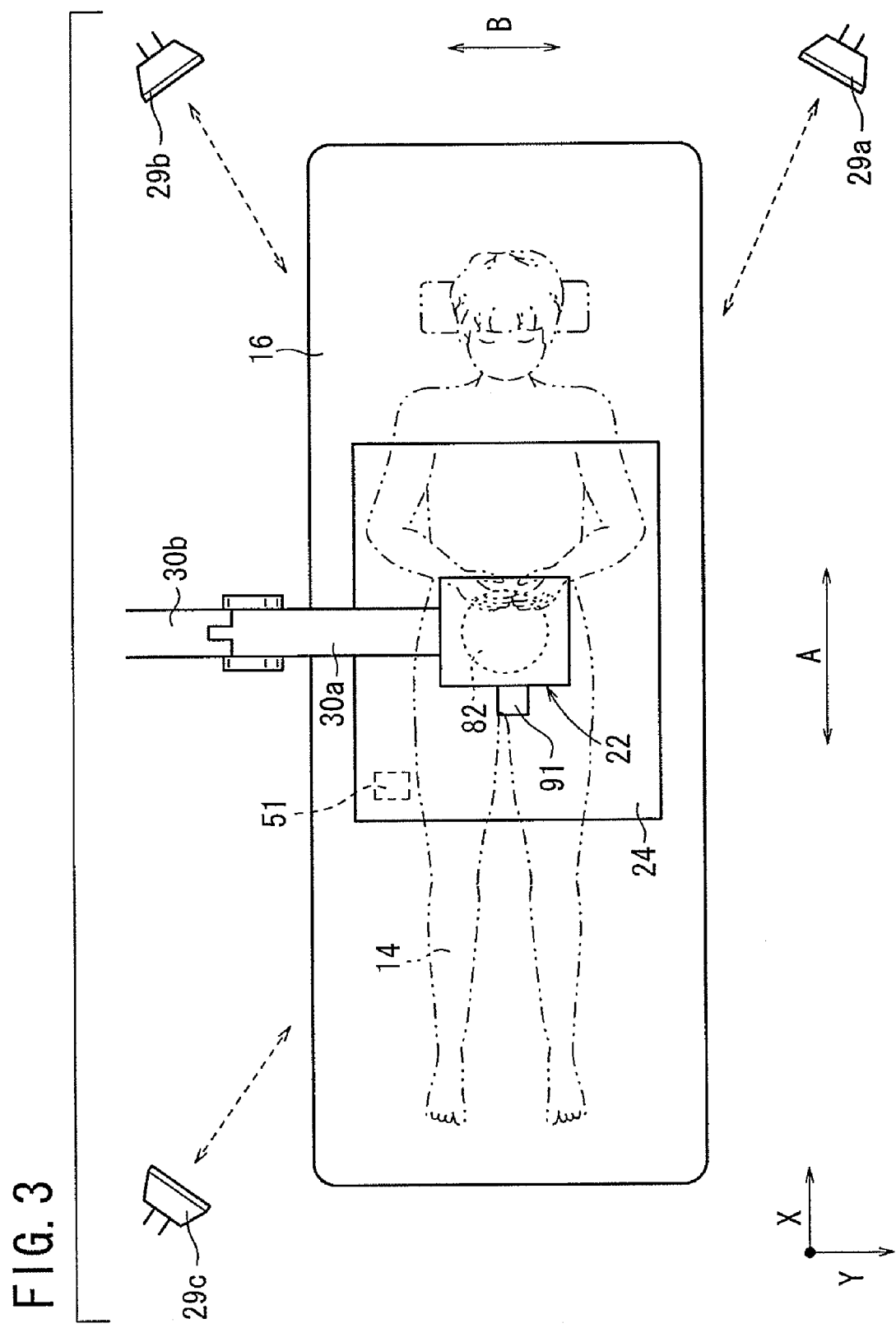
FIG. 3 is a plan view of the surgical table with the patient lying thereon in the operating room shown in FIG. 1.

FIGS. 1 through 3 show an operating room 12 incorporating a radiation image capturing system 10 according to an embodiment of the present invention. As shown in FIG. 1, the operating room 12 has, in addition to the radiation image capturing system 10, a surgical table 16 for a patient 14 to lie thereon, and an instrument table 20 disposed to one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus (image capturing unit) 22 for irradiating the patient 14 with a radiation X at a dosage according to image capturing conditions, a radiation detecting cassette 24 housing therein a radiation detector (radiation conversion panel) 40, to be described later, for detecting the radiation X that has passed through the patient 14, a display device 26 for displaying a radiation image based on the radiation X that is detected by the radiation detector 40, and a console 28 for controlling the image capturing apparatus 22, the radiation detecting cassette 24, and the display device 26. The image capturing apparatus 22, the radiation detecting cassette 24, the display device 26, and the console 28 transmit and receive signals by way of wireless communications.

The operating room 12 also has an antenna device (position detecting unit) 29 for detecting three-dimensional positions of the image capturing apparatus 22 and the radiation detecting cassette 24. The antenna device 29 comprises first, second, and third transceivers 29a, 29b, 29c each positioned in any one of the four corners of the operating room 12, for example, and connected to the console 28. The first, second, and third transceivers 29a, 29b, 29c are capable of transmitting radio waves to the image capturing apparatus 22 and the radiation detecting cassette 24, and of receiving radio waves from first and second receivers 51, 91 (see FIG. 3) disposed respectively in the image capturing apparatus 22 and the radiation detecting cassette 24.

The image capturing apparatus 22 is coupled to a plurality of universal arms 30a, 30b so as to be movable to a desired position for capturing an image at a desired area of the patient 14 and also to be retractable to a position out of the way while the surgeons 18 are performing a surgical operation on the patient 14. Similarly, the display device 26 is coupled to a universal arm 32 so as to be movable to a position where the surgeons 18 can easily confirm a captured radiation image displayed on the display device 26.

Figure 4:
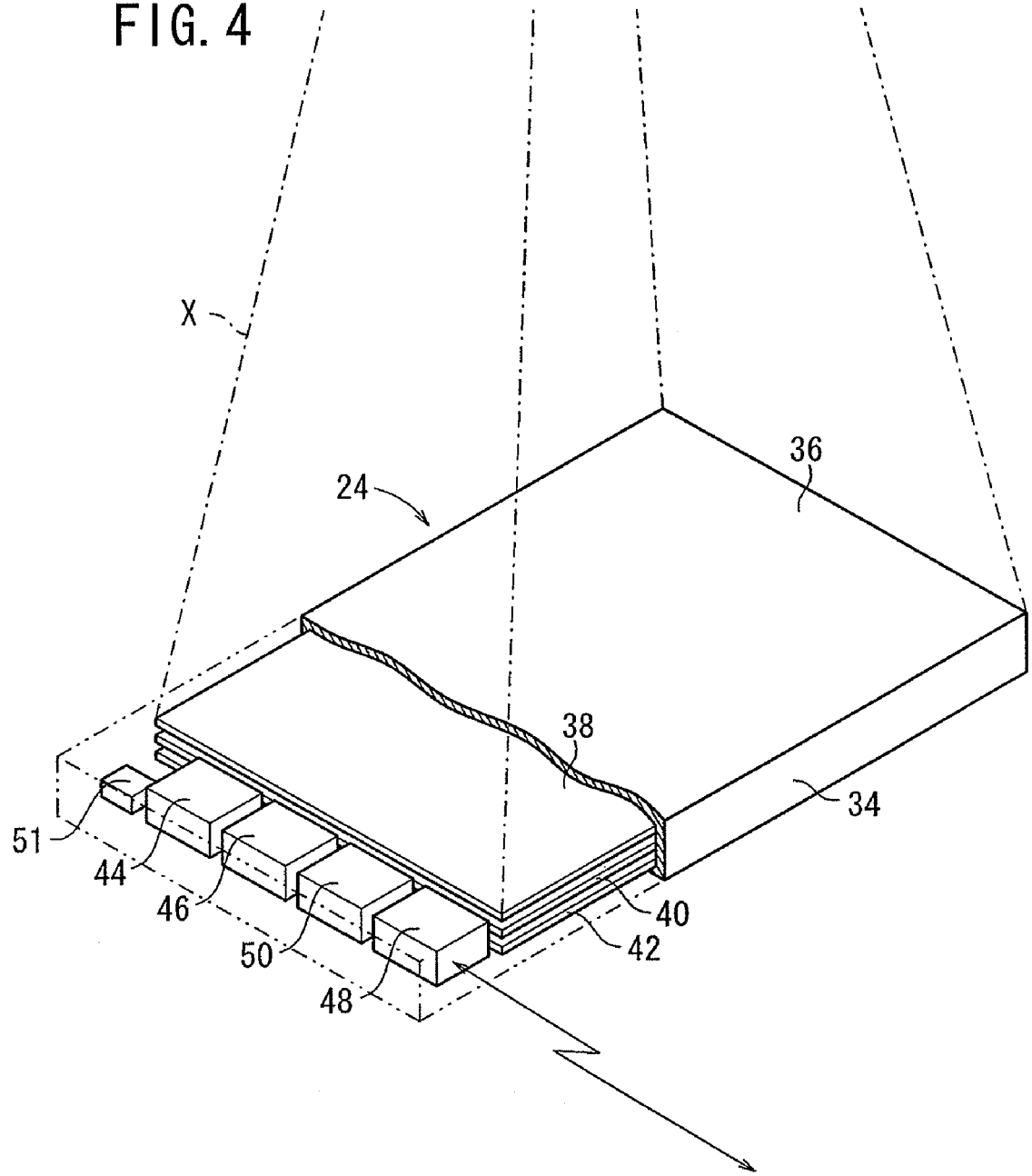
FIG. 4 is a perspective view, partly cut away, showing internal structural details of a radiation detecting cassette used in the radiation image capturing system.

FIG. 4 shows internal structural details of the radiation detecting cassette 24. As shown in FIG. 4, the radiation detecting cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays from the radiation X. The grid 38, the radiation detector 40 and the lead plate 42 are successively arranged in that order from a surface 36 of the casing 34 which is irradiated with the radiation X. The irradiated surface 36 of the casing 34 may be constructed as the grid 38.

The casing 34 also houses therein a battery 44 as a power supply of the radiation detecting cassette 24, a cassette controller 46 for energizing the radiation detector 40 with electric power supplied from the battery 44, a transceiver 48 for sending and receiving signals including the information of the radiation X detected by the radiation detector 40, to and from the console 28, a first detector 50 for detecting the direction, tilt, etc. of the radiation detecting cassette 24, and a first receiver (position detecting unit) 51 for receiving radio waves transmitted from the antenna device 29.

Figure 6:
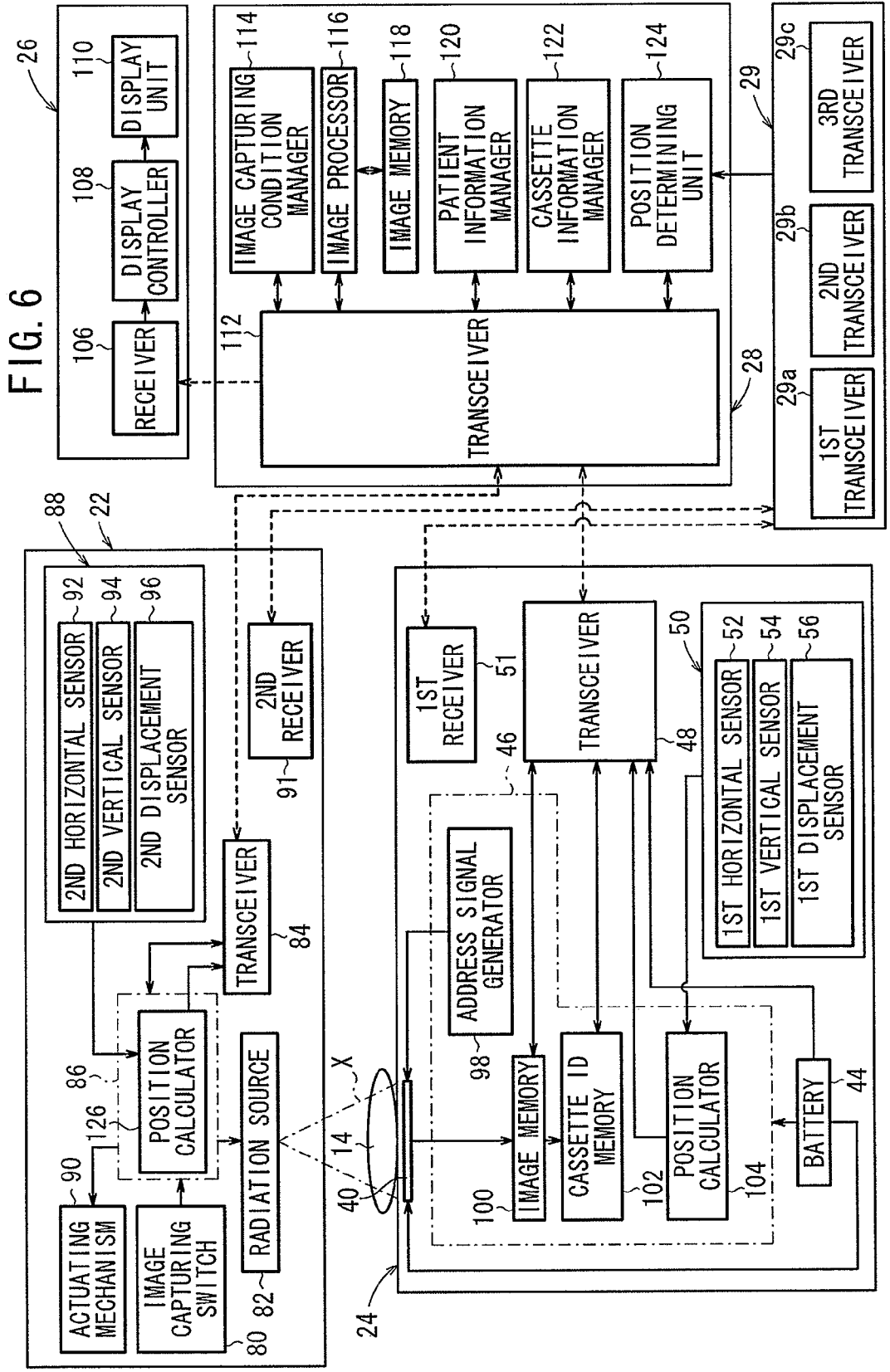
FIG. 6 is a block diagram of the radiation image capturing system.

As shown in FIG. 6, the first detector 50 comprises a first horizontal sensor 52 for detecting a horizontal position (in the directions indicated by the arrows A, B in FIG. 3) of the radiation detecting cassette 24 in the operating room 12, a first vertical sensor 54 for detecting a vertical position (in the directions indicated by the arrow C in FIG. 2) of the radiation detecting cassette 24 in the operating room 12, and a first displacement sensor 56 for detecting a displacement of the radiation detecting cassette 24.

The first horizontal sensor 52 comprises an azimuthal sensor for detecting a horizontal position in space based on geomagnetism, for example. The first vertical sensor 54 comprises a gravitational sensor. The first displacement sensor 56 comprises an acceleration sensor for detecting an acceleration generated when the radiation detecting cassette 24 is displaced.

As shown in FIG. 6, the first horizontal sensor 52, the first vertical sensor 54, and the first displacement sensor 56 of the first detector 50 output detected signals indicative of detected quantities to the cassette controller 46. The cassette controller 46 includes a position calculator 104, described later, which calculates the direction, tilt, etc. of the radiation detecting cassette 24 based on the detected signals.

The first horizontal sensor 52, the first vertical sensor 54, and the first displacement sensor 56, which have different characteristics, are thus combined to detect various quantities of the radiation detecting cassette 24, from which the direction, tilt, etc. of the radiation detecting cassette 24 can be detected accurately.

A shield plate of lead or the like such as the lead plate 42 should preferably be placed over the side surfaces of the cassette controller 46, the transceiver 48, the first detector 50, and the first receiver 51 under the irradiated surface 36 of the casing 34 to protect the cassette controller 46, the transceiver 48, the first detector 50, and the first receiver 51 against damage which would otherwise be caused if those were irradiated with the radiation X.

Figure 5:
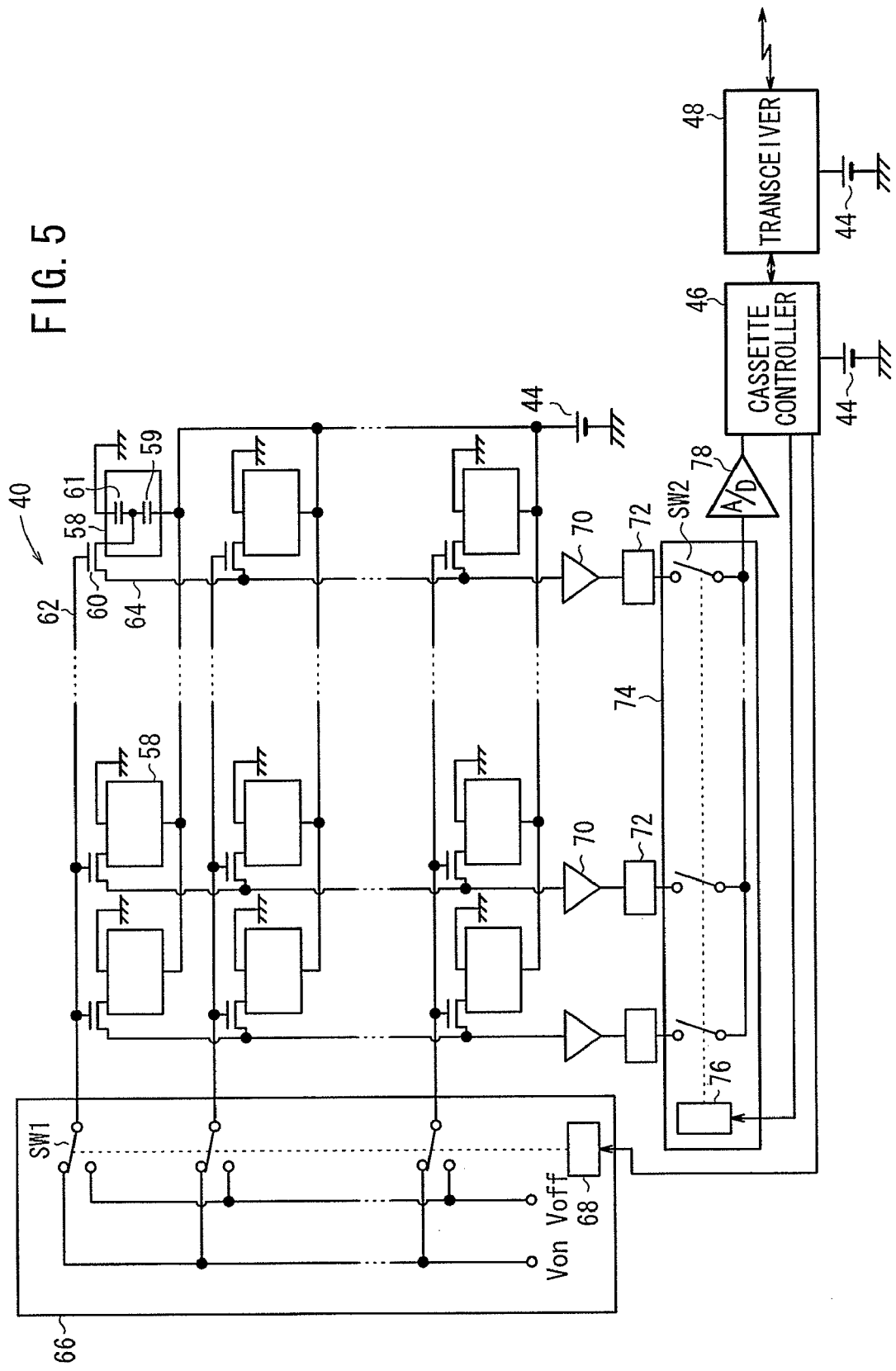
FIG. 5 is a block diagram of a circuit arrangement of a radiation detector.

FIG. 5 shows in block form a circuit arrangement of the radiation detector 40. As shown in FIG. 5, the radiation detector 40 comprises an array of thin-film transistors (TFTs) 60 arranged in rows and columns, a photoelectric conversion layer 59 made of a material such as amorphous selenium (a-Se) for generating electric charges upon detection of the radiation X, the photoelectric conversion layer 59 being disposed over the array of TFTs 60, and an array of storage capacitors 61 connected to the photoelectric conversion layer 59. When the radiation X is applied to the radiation detector 40, the photoelectric conversion layer 59 generates electric charges, and the storage capacitors 61 store the generated electric charges. Then, the TFTs 60 are turned on along each row at a time to read out the electric charges from the storage capacitors 61 as an image signal. In FIG. 5, the photoelectric conversion layer 59 and one of the storage capacitors 61 are shown as a pixel 58, and the pixel 58 is connected to one of the TFTs 60. Details of the other pixels 58 are omitted from illustration.

Since amorphous selenium tends to change its structure and lose its functionality at high temperatures, amorphous selenium needs to be used within a certain temperature range. Therefore, some means for cooling the radiation detector 40 should preferably be provided in the radiation detecting cassette 24.

The TFTs 60 connected to the respective pixels 58 are connected to respective gate lines 62 extending parallel to the rows and respective signal lines 64 extending parallel to the columns. The gate lines 62 are connected to a line scanning driver 66, and the signal lines 64 are connected to a multiplexer 74 serving as a reading circuit.

The gate lines 62 are supplied with control signals Von, Voff from the line scanning driver 66 for turning on and off the TFTs 60 along the rows. The line scanning driver 66 comprises a plurality of switches SW1 for switching between the gate lines 62 and an address decoder 68 for outputting a selection signal for selecting one of the switches SW1 at a time. The address decoder 68 is supplied with an address signal from the cassette controller 46.

The signal lines 64 are supplied with electric charges stored in the storage capacitors 61 of the pixels 58 through the TFTs 60 arranged in the columns. The electric charges supplied to the signal lines 64 are amplified by amplifiers 70 connected respectively to the signal lines 64. The amplifiers 70 are connected through respective sample and hold circuits 72 to the multiplexer 74. The multiplexer 74 comprises a plurality of switches SW2 for successively switching between the signal lines 64 and an address decoder 76 for outputting a selection signal for selecting one of the switches SW2 at a time. The address decoder 76 is supplied with an address signal from the cassette controller 46. The multiplexer 74 has an output terminal connected to an A/D converter 78. A radiation image signal generated by the multiplexer 74 based on the electric charges from the sample and hold circuits 72 is converted by the A/D converter 78 into a digital image signal representing radiation image information, which is supplied to the cassette controller 46.

FIG. 6 shows in block form the radiation image capturing system 10 which comprises the image capturing apparatus 22, the radiation detecting cassette 24, the display device 26, and the console 28.

The image capturing apparatus 22 comprises an image capturing switch 80, a radiation source 82 for outputting the radiation X, a transceiver 84 for receiving image capturing conditions from the console 28 by way of wireless communications and transmitting an image capturing completion signal, etc. to the console 28 by way of wireless communications, a radiation source controller 86 for controlling the radiation source 82 based on an image capturing start signal supplied from the image capturing switch 80 and image capturing conditions supplied from the transceiver 84, a second detector 88 for detecting the position of the image capturing apparatus 22, and an actuating mechanism (actuating unit) 90 for moving the image capturing apparatus 22 to a desired position based on the position detected by the second detector 88. A second receiver (position detecting unit) 91 for receiving radio waves transmitted from the antenna device 29 is mounted on a side wall of the image capturing apparatus 22.

The second detector 88 comprises a second horizontal sensor 92 for detecting a horizontal position (in the directions indicated by the arrows A, B in FIG. 3) of the image capturing apparatus 22 in the operating room 12, a second vertical sensor 94 for detecting a vertical position (in the directions indicated by the arrow C in FIG. 2) of the image capturing apparatus 22 in the operating room 12, and a second displacement sensor 96 for detecting a displacement of the image capturing apparatus 22, for example, as with the first detector 50 shown above.

The second horizontal sensor 92 comprises an azimuthal sensor for detecting a horizontal position in space based on geomagnetism, for example. The second vertical sensor 94 comprises a gravitational sensor. The second displacement sensor 96 comprises an acceleration sensor for detecting an acceleration generated when the image capturing apparatus 22 is displaced.

The second horizontal sensor 92, the second vertical sensor 94, and the second displacement sensor 96 of the second detector 88 output detected signals indicative of detected quantities to the radiation source controller 86. The radiation source controller 86 includes a position calculator 126, described later, which calculates the direction, tilt, etc. of the image capturing apparatus 22 based on the supplied detected signals.

The second horizontal sensor 92, the second vertical sensor 94, and the second displacement sensor 96, which have different characteristics, are thus combined to detect various quantities of the image capturing apparatus 22, from which the direction, tilt, etc. of the image capturing apparatus 22 can be detected by the position calculator 126.

The actuating mechanism 90 comprises stepping motors, actuators, or the like which are disposed in junctions of the universal arms 30a, 30b for tilting the universal arms 30a, 30b relatively to each other for universally moving the image capturing apparatus 22. The actuating mechanism 90 is electrically connected to the radiation source controller 86, and can be energized by a control signal output from the radiation source controller 86 to move the image capturing apparatus 22 to a desired position.

The radiation detecting cassette 24 houses therein the radiation detector 40, the battery 44, the cassette controller 46, the transceiver 48, the first detector 50, and the first receiver 51.

The cassette controller 46 comprises an address signal generator 98 for supplying address signals to the address decoder 68 of the line scanning driver 66 and the address decoder 76 of the multiplexer 74 of the radiation detector 40, an image memory 100 for storing the radiation image information detected by the radiation detector 40, a cassette ID memory 102 for storing cassette ID information for identifying the radiation detecting cassette 24, and the position calculator 104 for calculating the position of the radiation detecting cassette 24 in the operating room 12 based on the detected quantities from the first detector 50.

The transceiver 48 receives a transmission request signal from the console 28 by way of wireless communications and transmits the cassette ID information stored in the cassette ID memory 102, the radiation image information stored in the image memory 100, and the information representing the direction, tilt, etc. of the radiation detecting cassette 24 detected by the first detector 50, to the console 28 by way of wireless communications.

The display device 26 comprises a receiver 106 for receiving radiation image information from the console 28, a display controller 108 for controlling the display of the received radiation image information, and a display unit (warning unit) 110 for displaying the radiation image information processed by the display controller 108.

The console 28 comprises a transceiver 112 for transmitting and receiving necessary information including radiation image information, positional information, etc. to and from the image capturing apparatus 22, the radiation detecting cassette 24, and the display device 26 by way of wireless communications, an image capturing condition manager 114 for managing image capturing conditions required for the image capturing apparatus 22 to capture radiation images, an image processor 116 for processing radiation image information transmitted from the radiation detecting cassette 24, an image memory 118 for storing the radiation image information processed by the image processor 116, a patient information manager 120 for managing patient information of the patient 14 whose images are to be captured, a cassette information manager 122 for managing cassette information transmitted from the radiation detecting cassette 24, and a position determining unit 124 for determining the relative positional relationship between the image capturing apparatus 22 and the radiation detecting cassette 24 based on the propagation times "t" of radio waves that are transmitted from the antenna device 29 to the image capturing apparatus 22 and the radiation detecting cassette 24.

The console 28 may be located outside of the operating room 12 insofar as it can transmit and receive signals to and from the image capturing apparatus 22, the radiation detecting cassette 24, and the display device 26 by way of wireless communications.

The position determining unit 124 is supplied, through the transceivers 48, 84, 112, with positional information of the image capturing apparatus 22 and the radiation detecting cassette 24 which is detected based on the differences between the propagation times "t" of radio waves detected by the antenna device 29 which includes the first, second, and third transceivers 29a, 29b, 29c, and compares the relative positions of the image capturing apparatus 22 and the radiation detecting cassette 24 with each other.

The position determining unit 124 determines whether or not the radiation detecting cassette 24 and the image capturing apparatus 22 are positioned in vertically head-on facing relation to each other. If the radiation detecting cassette 24 and the image capturing apparatus 22 are not positioned in vertically head-on facing relation to each other, i.e., if they are not vertically aligned with each other, then the position determining unit 124 outputs a control signal through the transceiver 112 to the radiation source controller 86, which energizes the actuating mechanism 90.

Therefore, the position determining unit 124 functions as a determining means for determining whether or not the radiation detecting cassette 24 and the image capturing apparatus 22 are positioned in vertically head-on facing relation to each other. The positional information of the image capturing apparatus 22 and the radiation detecting cassette 24 is expressed as XYZ coordinates, for example.

When the radiation detecting cassette 24 and the image capturing apparatus 22 are positioned in vertically head-on facing relation to each other, the radiation detecting cassette 24 is positioned directly below (vertically downwardly of) the image capturing apparatus 22 as it is viewed from above (see FIG. 3). Stated otherwise, if it is assumed that the surgical table 16 has its longitudinal direction extending along an X-axis, its transverse direction extending along a Y-axis, and its vertical direction extending along a Z-axis, then the center of the radiation detecting cassette 24 and the radiation source 82 at the center of the image capturing apparatus 22 are aligned with each other in an XY plane defined by the X-axis and the Y-axis, and are spaced from each other by a certain distance only in the vertical direction (indicated by the arrow C) along the Z-axis (see FIG. 2).

The radiation image capturing system 10 according to the present embodiment is basically constructed as described above, and operation of the radiation image capturing system 10 will be described below.

The radiation image capturing system 10 is installed in the operating room 12 and used when a radiation image of the patient 14 is required by the surgeons 18 who are performing an operation on the patient 14. Before a radiation image of the patient 14 is captured, patient information of the patient 14 to be imaged is registered in the patient information manager 120 of the console 28. If an area of the patient 14 to be imaged and an image capturing method have already been known, they are registered as image capturing conditions in the image capturing condition manager 114. After the above preparatory process is finished, the surgeons 18 perform an operation on the patient 14.

For capturing a radiation image of the patient 14 during the operation, one of the surgeons 18 or the radiological technician places the radiation detecting cassette 24 in a given position between the patient 14 and the surgical table 16 with the irradiated surface 36 facing the image capturing apparatus 22.

At this time, the first, second, and third transceivers 29a, 29b, 29c of the antenna device 29 emit radio waves, which are received by the first receiver 51 housed in the radiation detecting cassette 24 and the second receiver 91 mounted on the image capturing apparatus 22. The position determining unit 124 of the console 28 calculates the propagation times "t" of the radio waves emitted from the respective the first, second, and third transceivers 29a, 29b, 29c, from the time the radio waves are emitted until they are received by the first and second receivers 51, 91, and specifies the positions of the first and second receivers 51, 91 in the operating room 12 based on the differences between the propagation times "t". In other words, the position determining unit 124 calculates the relative positions of the radiation detecting cassette 24 having the first receiver 51 and the image capturing apparatus 22 having the second receiver 91.

Then, based on the positional relationship between the image capturing apparatus 22 and the radiation detecting cassette 24 in the operating room 12, the position determining unit 124 determines whether or not the image capturing apparatus 22 is positioned upwardly of the radiation detecting cassette 24 in vertically head-on facing relation thereto in the direction indicated by the arrow C. Stated otherwise, the position determining unit 124 determines whether the image capturing apparatus 22 has been moved to and disposed in a given position which faces the affected part of the patient 14 head-on.

If the position determining unit 124 judges that the image capturing apparatus 22 is positioned upwardly of the radiation detecting cassette 24 in vertically head-on facing relation thereto, then the first horizontal sensor 52, the first vertical sensor 54, and the first displacement sensor 56 of the first detector 50 detect the direction, tilt etc. of the radiation detecting cassette 24. At the same time, the second horizontal sensor 92, the second vertical sensor 94, and the second displacement sensor 96 of the second detector 88 detect the direction, tilt, etc. of the image capturing apparatus 22. The first detector 50 outputs detected signals indicative of the detected quantities to the position calculator 104 of the cassette controller 46, and the second detector 88 outputs detected signals indicative of the detected quantities to the position calculator 126 of the radiation source controller 86. The position calculators 104, 126 then calculate the directions, tilts, etc. of the image capturing apparatus 22 and the radiation detecting cassette 24. The information representing the calculated directions, tilts, etc. is transmitted from the position calculators 104, 126 through the transceivers 48, 84 to the console 28. In the console 28, the transmitted information is supplied through the transceiver 112 to the position determining unit 124.

The position determining unit 124 now confirms that the image capturing apparatus 22 and the radiation detecting cassette 24 are facing each other head-on in one direction without being tilted with respect to each other.

After having confirmed that the image capturing apparatus 22 and the radiation detecting cassette 24 are facing each other head-on, one of the surgeons 18 or the radiological technician turns on the image capturing switch 80 to capture a radiation image of the patient 14. The radiation source controller 86 of the image capturing apparatus 22 acquires the image capturing conditions for the area of the patient 14 to be imaged from the image capturing condition manager 114 of the console 28 through the transceivers 84, 112 by way of wireless communications, and controls the radiation source 82 according to the acquired image capturing conditions to apply a radiation X at a given dosage to the patient 14.

Based on the positional information of the image capturing apparatus 22 and the radiation detecting cassette 24, if the position determining unit 124 judges that the image capturing apparatus 22 is not positioned upwardly of the radiation detecting cassette 24 in vertically head-on facing relation thereto, then it is determined that the radiation X from the image capturing apparatus 22 will not be applied to the affected area of the patient 14 and the radiation detector 40 of the radiation detecting cassette 24, and a desired radiation image of the affected area of the patient 14 will not be captured. Based on the determination, the position determining unit 124 gives the console 28, the display device 26, etc. a warning indicating that the image capturing apparatus 22 including the radiation source 82 and the radiation detecting cassette 24 are not placed in the desired position.

At the same time, the position determining unit 124 outputs a control signal through the transceivers 112, 84 to the radiation source controller 86, which outputs an actuating signal to the actuating mechanism 90. In response to the actuating signal, the actuating mechanism 90 turns the universal arms 30a, 30b through respective given angles to move the image capturing apparatus 22 on the end of the universal arm 30a to a position which faces the radiation detecting cassette 24 head-on.

The distance that the image capturing apparatus 22 is to travel at this time is determined based on the difference between the positional information of the radiation detecting cassette 24 and the positional information of the image capturing apparatus 22. The actuating signal output from the radiation source controller 86 to the actuating mechanism 90 is based on the difference between the positional information of the radiation detecting cassette 24 and the positional information of the image capturing apparatus 22.

After the image capturing apparatus 22 has moved the given distance, the relative positional relationship between the image capturing apparatus 22 and the radiation detecting cassette 24 is confirmed again based on radio waves emitted from the antenna device 29 and received by the first and second receivers 51, 91. After having confirmed again that the image capturing apparatus 22 and the radiation detecting cassette 24 are facing each other head-on, one of the surgeons 18 or the radiological technician turns on the image capturing switch 80 to capture a radiation image of the patient 14. At this time, the first and second detectors 50, 88 also detect the directions, tilts, etc. of the radiation detecting cassette 24 and the image capturing apparatus 22 for the position determining unit 124 to confirm that the image capturing apparatus 22 and the radiation detecting cassette 24 are facing each other head-on in one direction without being tilted with respect to each other.

The radiation X which has been applied from the radiation source 82 to the patient 14 and has passed through the patient 14 is applied to the grid 38 of the radiation detecting cassette 24, which removes scattered rays of the radiation X. Then, the radiation X is applied to the radiation detector 40, and converted into electric signals by the photoelectric conversion layer 59 of the pixels 58 of the radiation detector 40. The electric signals are stored as electric charges in the storage capacitors 61 (see FIG. 5). The stored electric charges in the storage capacitors 61, which represent radiation image information of the patient 14, are read out from the storage capacitors 61 according to address signals which are supplied from the address signal generator 98 of the cassette controller 46 to the line scanning driver 66 and the multiplexer 74.

Specifically, in response to the address signal supplied from the address signal generator 98, the address decoder 68 of the line scanning driver 66 outputs a selection signal to select one of the switches SW1, which supplies the control signal Von to the gates of the TFTs 60 connected to the gate line 62 corresponding to the selected switch SW1. In response to the address signal supplied from the address signal generator 98, the address decoder 76 of the multiplexer 74 outputs a selection signal to successively turn on the switches SW2 to switch between the signal lines 64 for thereby reading out the electric charges stored in the storage capacitors 61 of the pixels 58 connected to the selected gate line 62 that is selected by the line scanning driver 66, through the signal lines 64.

The electric charges read out from the storage capacitors 61 of the pixels 58 connected to the selected gate line 62 are amplified by the respective amplifiers 70, sampled by the sample and hold circuits 72, and supplied to the multiplexer 74. Based on the supplied electric charges, the multiplexer 74 generates and supplies a radiation image signal to the A/D converter 78, which converts the radiation image signal into a digital signal. The digital signal which represents the radiation image information is stored in the image memory 100 of the cassette controller 46, and thereafter transmitted from the transceiver 48 to the console 28 by way of wireless communications.

Similarly, the address decoder 68 of the line scanning driver 66 successively turns on the switches SW1 to switch between the gate lines 62 according to the address signal supplied from the address signal generator 98. The electric charges stored in the storage capacitors 61 of the pixels 58 connected to the successively selected gate lines 62 are read out through the signal lines 64, and processed by the multiplexer 74 and the A/D converter 78 into digital signals, which are stored in the image memory 100 of the cassette controller 46.

The radiation image information transmitted to the console 28 is received by the transceiver 112, processed by the image processor 116, and then stored in the image memory 118 in association with the patient information of the patient 14 registered in the patient information manager 120.

The radiation image information processed by the image processor 116 is transmitted from the transceiver 112 to the display device 26. In the display device 26, the receiver 106 receives the radiation image information, and the display controller 108 controls the display unit 110 to display a radiation image based on the radiation image information. The surgeons 18 perform a surgical operation on the patient 14 while watching the radiation image displayed on the display unit 110.

Since no cables for transmitting and receiving signals are connected between the radiation detecting cassette 24 and the console 28, between the image capturing apparatus 22 and the console 28, and between the console 28 and the display device 26, it is not necessary to lay such cables on the floor of the operating room 12 and hence there are no cable-induced obstacles to the operation performed by the surgeons 18, the radiological technician, or other staff members in the operating room 12.

In the above embodiment, the first and second displacement sensors 56, 96 of the first and second detectors 50, 88 comprise acceleration sensors as described above. However, the first and second displacement sensors 56, 96 may comprise gyro sensors. If the first and second displacement sensors 56, 96 comprise gyro sensors, then they can detect angular displacements of the image capturing apparatus 22 and the radiation detecting cassette 24, and the detected angular displacements may be combined with the detected signals from the first and second horizontal sensors 52, 92 and the first and second vertical sensors 54, 94 to detect directions, tilts, etc. of the image capturing apparatus 22 and the radiation detecting cassette 24.

In the above embodiment, furthermore, the antenna device 29 comprising the first, second, and third transceivers 29a, 29b, 29c is disposed in the operating room 12, and the first and second receivers 51, 91 are combined with the image capturing apparatus 22 and the radiation detecting cassette 24, respectively, for specifying the positions of the image capturing apparatus 22 and the radiation detecting cassette 24. However, the present invention is not limited to such a configuration. Base stations for transmitting and receiving UWB (Ultra Wide Band) signals may be combined with the image capturing apparatus 22 and the console 28, respectively, and a UWB receiver such as a tag, for example, for receiving such UWB signals may be housed in the radiation detecting cassette 24. According to such a modification, the propagation times of UWB signals from the UWB receiver to the base stations may be calculated, and the position of the radiation detecting cassette 24 with the UWB receiver may be specified based on the difference between the calculated propagation times.

If the transceiver 48 in the radiation detecting cassette 24 comprises a transceiver capable of UWB communications, then the radiation detecting cassette 24 needs no separate UWB receiver, but the transceiver 48 can also be used to transmit and receive UWB signals.

According to the above embodiment, as described above, the position of the image capturing apparatus 22 including the radiation source 82 and the position of the radiation detecting cassette 24 housing the radiation detector 40 are detected by the antenna device 29 and the first and second receivers 51, 91 which serve as the position detecting unit. Based on the detected positional information, the position determining unit 124 of the console 28 determines whether or not the image capturing apparatus 22 and the radiation detecting cassette 24 face each other head-on. Consequently, it is possible to recognize in advance when the image capturing apparatus 22 does not face the radiation detecting cassette 24 head-on and cannot capture a radiation image of the patient 14 properly.

If the image capturing apparatus 22 does not face the radiation detecting cassette 24 head-on and cannot capture a radiation image of the patient 14 properly, then the actuating mechanism 90 of the image capturing apparatus 22 can move the image capturing apparatus 22 to a position which faces the radiation detecting cassette 24 head-on. Therefore, the image capturing apparatus 22 and the radiation detecting cassette 24 can reliably and accurately be placed in respective positions for capturing a radiation image. In addition, as wrong radiation images are prevented from being captured when the image capturing apparatus 22 and the radiation detecting cassette 24 are not properly positioned relatively to each other, proper radiation images can be captured highly efficiently.

When the radiation image capturing system 10 is in actual use, the position determining unit 124 may determine whether or not the radiation detecting cassette 24 and the image capturing apparatus 22 face each other head-on according to a rough criterion. In such a case, an optimum criterion may be used for the position determining unit 124 to determine whether or not the radiation detecting cassette 24 and the image capturing apparatus 22 face each other head-on.

Another embodiment of the present invention will be described below with reference to FIGS. 7 through 9. According to the other embodiment, the surgical table 16 in the operating room 12 incorporating the radiation image capturing system 10 shown in FIG. 1 is replaced with a stretcher 150 (see FIG. 7) that can be moved into the operating room 12 with the patient 14 lying thereon.

Figure 7:
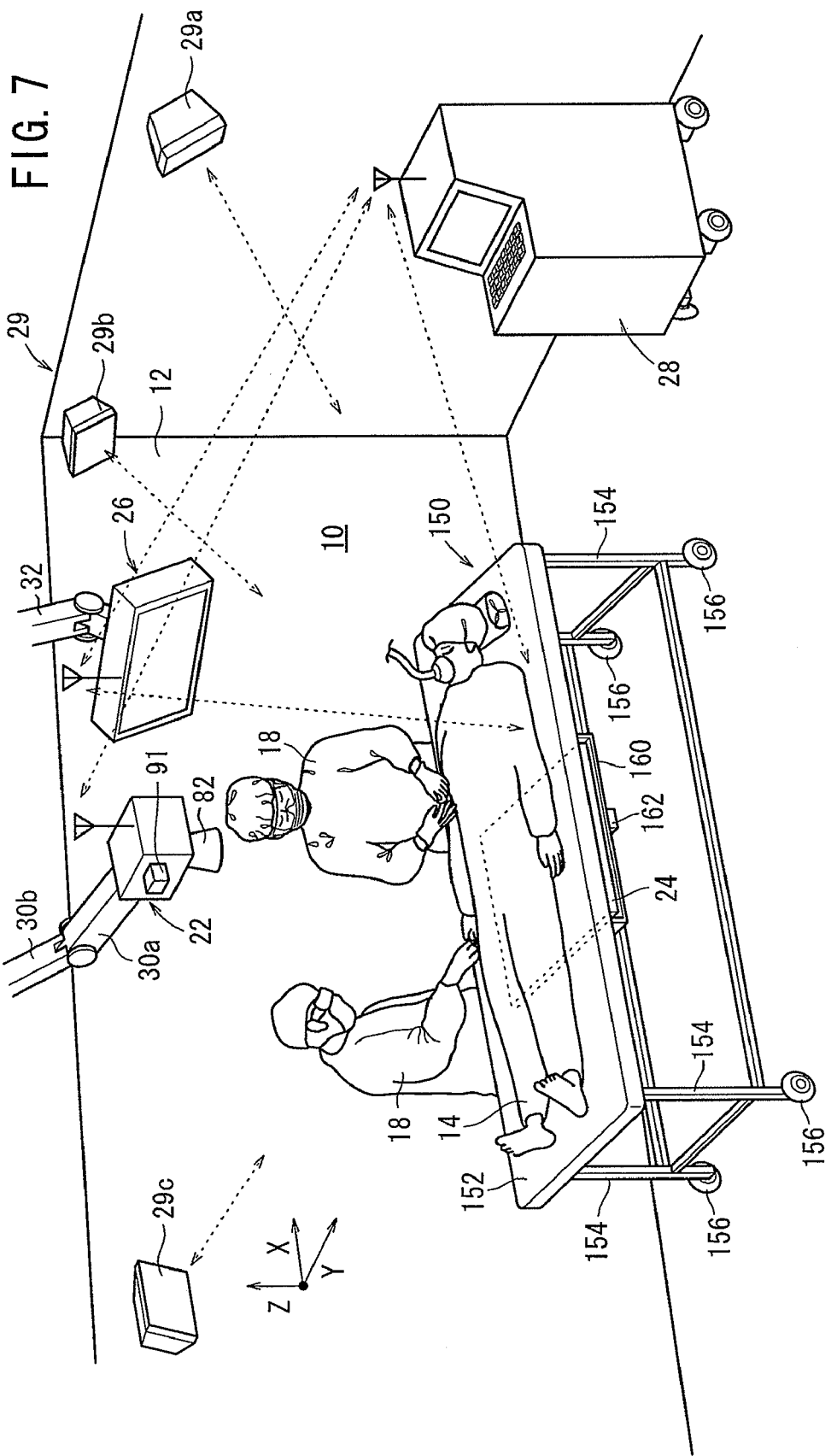
FIG. 7 is a perspective view inside the operating room incorporating the radiation image capturing system shown in FIG. 1, with the surgical table being replaced with a movable stretcher which can accommodate therein a radiation detecting cassette according to another embodiment of the present invention.
Figure 8:
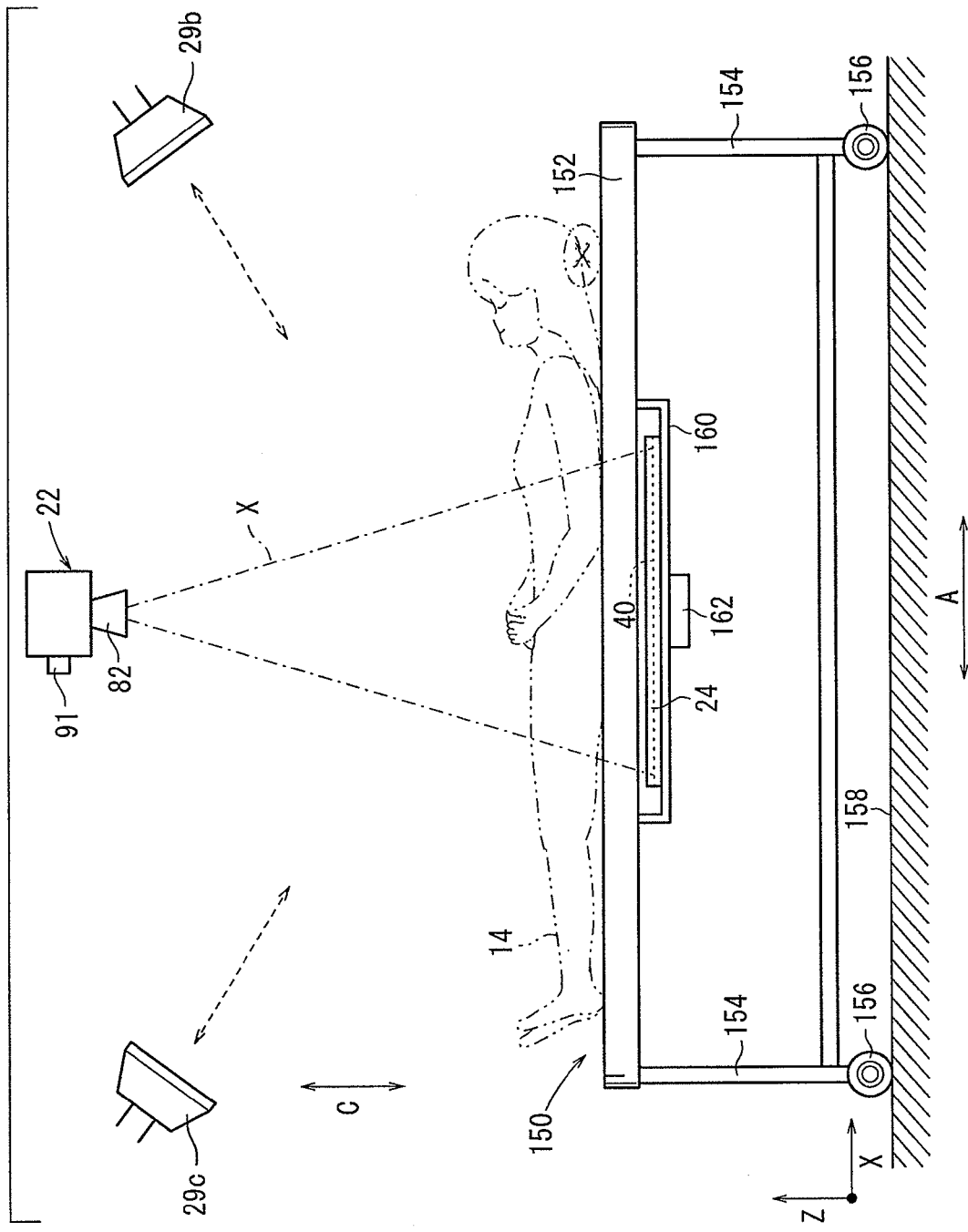
FIG. 8 is a side elevational view of the movable stretcher with the patient lying thereon in the operating room shown in FIG. 7.
Figure 9:
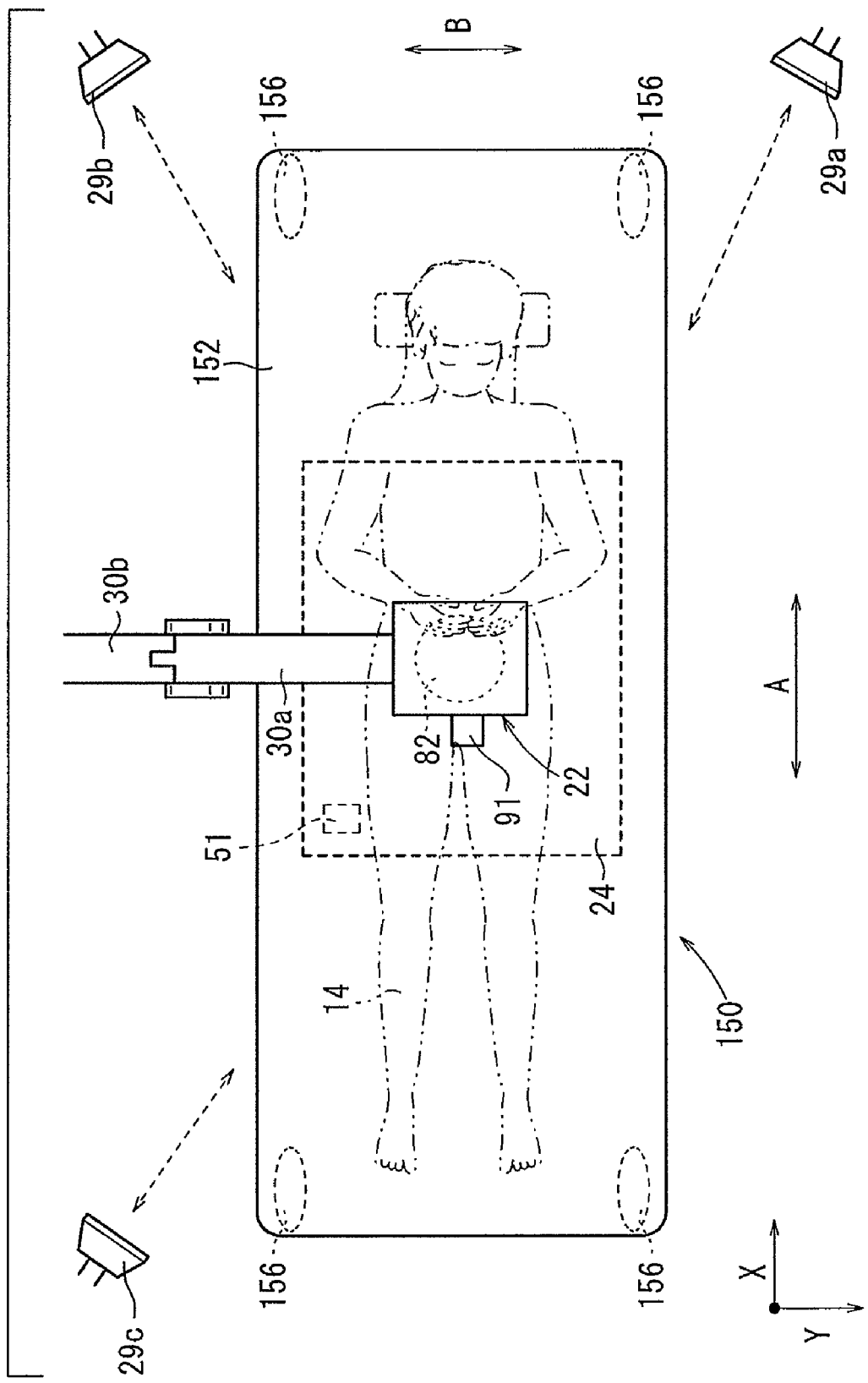
FIG. 9 is a plan view of the movable stretcher with the patient lying thereon in the operating room shown in FIG. 7.

As shown in FIGS. 7 through 9, the stretcher 150 comprises a bed 152 for the patient 14 to lie on an upper surface thereof, four legs 154 extending downwardly from the respective four corners of the bed 152, and casters 156 rotatably mounted on the respective lower ends of the legs 154. The casters 156 are rotatable on a floor 158 to move the bed 152 with the patient 14 lying thereon.

The bed 152 has a cassette holder 160 mounted on a lower surface thereof for housing the radiation detecting cassette 24 therein. The cassette holder 160 mounted on the lower surface of the bed 152 faces the floor 158 and has a space therein which is open laterally of the bed 152. The cassette holder 160 is movable along the bed 152 in the longitudinal directions thereof indicated by the arrow A, with the radiation detecting cassette 24 being housed in the space thereof. The position of the cassette holder 160, i.e., the radiation detecting cassette 24 with respect to the bed 152 can be changed depending on the area of the patient 14 to be imaged.

The cassette holder 160 has a third receiver (position detecting unit) 162 mounted centrally on a lower surface thereof for receiving radio waves emitted from the antenna device 29.

For capturing a radiation image of the patient 14, the cassette holder 160 is positionally adjusted to a position vertically aligned with the area of the patient 14 to be imaged, and then the stretcher 150 with the patient 14 lying thereon is moved into the operating room 12. The first, second, and third transceivers 29a, 29b, 29c of the antenna device 29 emit radio waves, which are received by the second receiver 91 mounted on the image capturing apparatus 22 and the third receiver 162 mounted on the cassette holder 160.

The position determining unit 124 of the console 28 calculates the propagation times "t" of the radio waves emitted from the respective the first, second, and third transceivers 29a, 29b, 29c, from the time the radio waves are emitted until they are received by the second and third receivers 91, 162, and specifies the positions of the second and third receivers 91, 162 in the operating room 12 based on the differences between the propagation times "t".

Then, based on the positions of the image capturing apparatus 22 and the cassette holder 160 in the operating room 12, the position determining unit 124 calculates the relative positions of the image capturing apparatus 22 having the second receiver 91 and the cassette holder 160 having the third receiver 162, and determines whether or not the image capturing apparatus 22 is positioned upwardly of the cassette holder 160 in vertically head-on facing relation thereto.

If the position determining unit 124 confirms that the image capturing apparatus 22 is positioned upwardly of the cassette holder 160 in vertically head-on facing relation thereto, then the radiation detecting cassette 24 is inserted into the cassette holder 160, and a radiation image of the patient 14 is captured in the radiation detecting cassette 24.

If the position determining unit 124 judges that the image capturing apparatus 22 is not positioned upwardly of the cassette holder 160 in vertically head-on facing relation thereto, then the position determining unit 124 gives the console 28, the display device 26, etc. a warning indicating that the image capturing apparatus 22 and the cassette holder 160 are not placed in the desired position.

Accordingly, the cassette holder 160 and the image capturing apparatus 22 can be placed in head-on facing relation to each other before the radiation detecting cassette 24 is inserted into the cassette holder 160. Therefore, it is possible to confirm quickly whether the image capturing apparatus 22 is positioned upwardly of the cassette holder 160 in vertically head-on facing relation thereto irrespectively of whether or not the radiation detecting cassette 24 is installed in position at the time the stretcher 150 is brought into the operating room 12.

The radiation detecting cassette 24 may be inserted into the cassette holder 160 before the stretcher 150 is brought into the operating room 12. If the radiation detecting cassette 24 is inserted into the cassette holder 160 before the stretcher 150 is brought into the operating room 12, then it is determined whether or not the image capturing apparatus 22, the radiation detecting cassette 24, and the cassette holder 160 are positioned in vertically head-on facing relation to each other based on the radio waves emitted from the first, second, and third transceivers 29a, 29b, 29c.

Still another embodiment of the present invention will be described below with reference to FIGS. 10 and 11. According to the still other embodiment, a surgical table 200 with the radiation detecting cassette 24 being placed on one side thereof is installed in the operating room 12 incorporating the radiation image capturing system 10 shown in FIG. 1.

Figure 10:
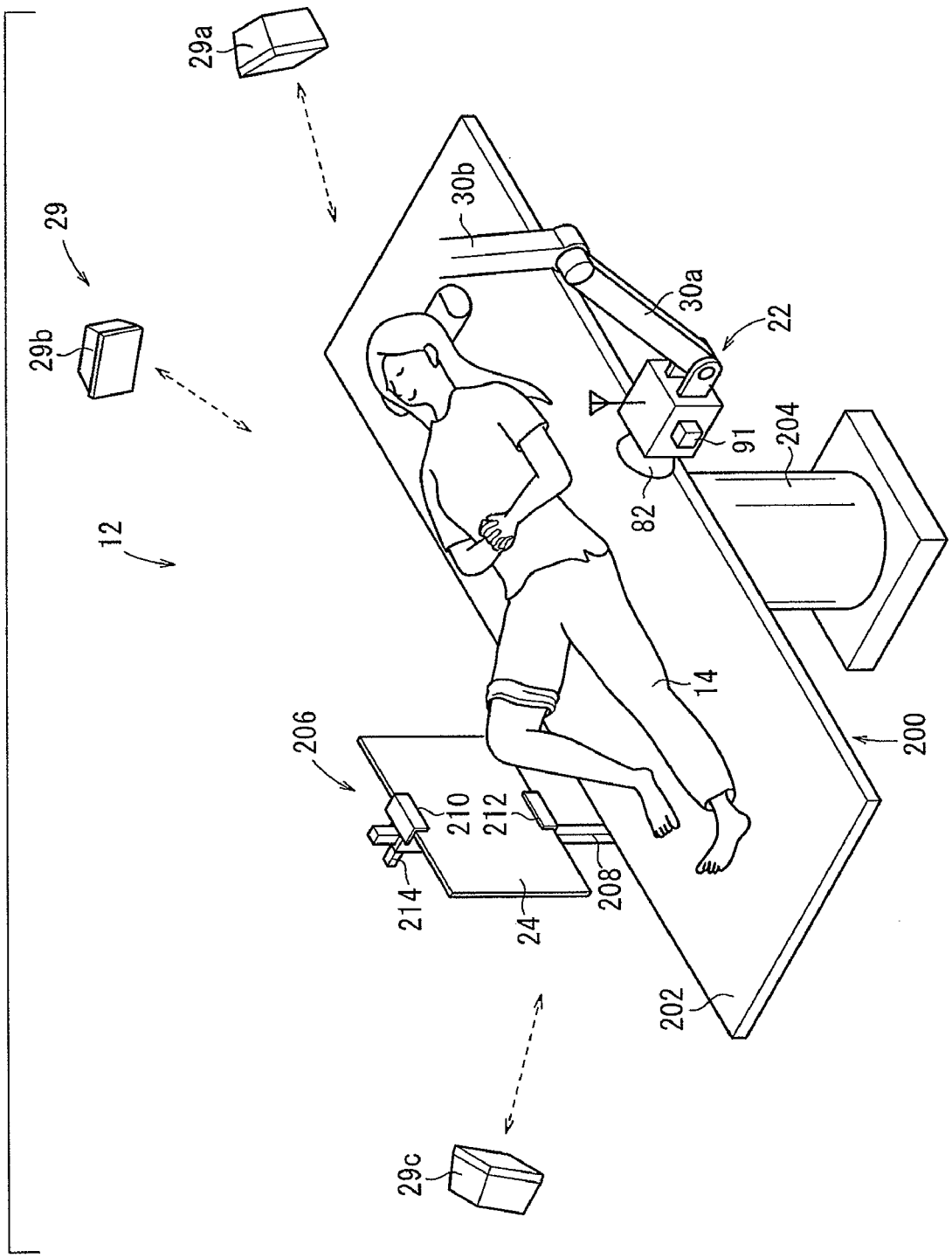
FIG. 10 is a schematic perspective view inside the operating room including a surgical table which is capable of holding a radiation detecting cassette on one side thereof according to still another embodiment of the present invention.
Figure 11:
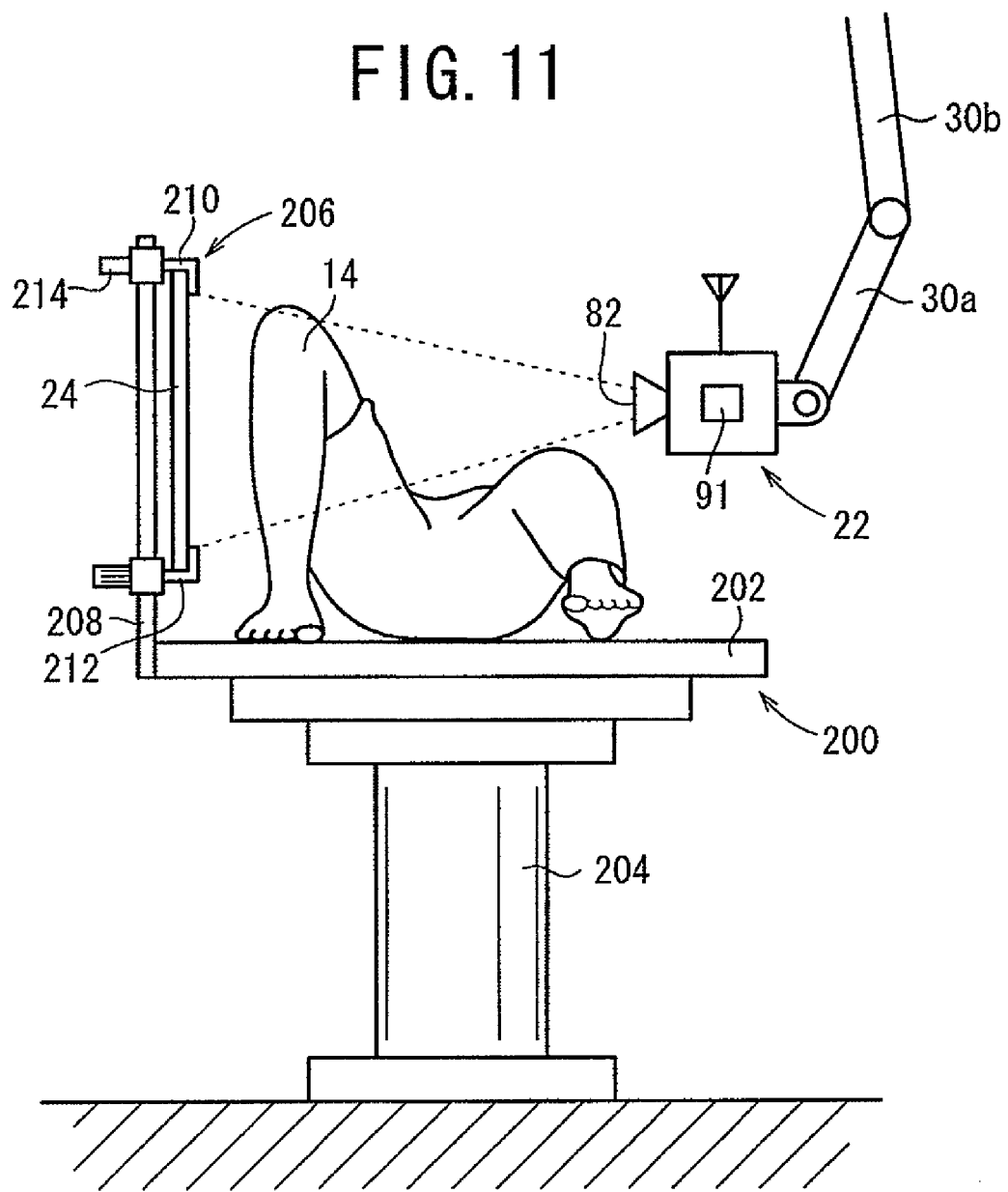
FIG. 11 is an end elevational view of the operating room shown in FIG. 10 as viewed from the feet of the patient.

As shown in FIGS. 10 and 11, the surgical table 200 comprises a bed 202 for the patient 14 to lie on an upper surface thereof, a leg 204 erected from the floor and supporting the bed 202 on its upper end, and a cassette holder 206 mounted on one side of the bed 202 for holding the radiation detecting cassette 24.

The cassette holder 206 comprises a post 208 fixed to the side of the bed 202 and extending upwardly perpendicularly to the horizontal plane of the bed 202, a first holder 210 mounted on an upper portion of the post 208, a second holder 212 displaceably mounted on a lower portion of the post 208, and a fourth receiver (position detecting unit) 214 mounted on an upper end of the post 208 for receiving radio waves emitted from the antenna device 29. The radiation detecting cassette 24 is held by the cassette holder 206 as follows: The radiation detecting cassette 24 is positioned between the first and second holders 210, 212 in front of the post 208, and has an upper edge held against the first holder 210. Then, the second holder 212 is displaced along the post 208 into abutment against a lower edge of the radiation detecting cassette 24, whereupon the radiation detecting cassette 24 is gripped between the first and second holders 210, 212.

For capturing a radiation image of the patient 14, the cassette holder 206 is positionally adjusted to a position horizontally aligned with the area of the patient 14 (e.g., a knee region) to be imaged. The first, second, and third transceivers 29a, 29b, 29c of the antenna device 29 emit radio waves, which are received by the second receiver 91 mounted on the image capturing apparatus 22 and the fourth receiver 214 of the cassette holder 206. The position determining unit 124 of the console 28 calculates the propagation times "t" of the radio waves emitted from the respective the first, second, and third transceivers 29a, 29b, 29c, from the time the radio waves are emitted until they are received by the second and fourth receivers 91, 214, and specifies the positions of the second and fourth receivers 91, 214 in the operating room 12 based on the differences between the propagation times "t".

Then, based on the positions of the image capturing apparatus 22 and the cassette holder 206 in the operating room 12, the position determining unit 124 calculates the relative positions of the image capturing apparatus 22 having the second receiver 91 and the cassette holder 206 having the fourth receiver 214, and determines whether or not the image capturing apparatus 22 is positioned laterally of the cassette holder 206 in horizontally head-on facing relation thereto.

If the position determining unit 124 confirms that the image capturing apparatus 22 is positioned laterally of the cassette holder 206 in horizontally head-on facing relation thereto, then the radiation detecting cassette 24 is set on the cassette holder 206, and a radiation image of the patient 14 is captured in the radiation detecting cassette 24.

If the position determining unit 124 judges that the image capturing apparatus 22 is not positioned laterally of the cassette holder 206 in horizontally head-on facing relation thereto, then the position determining unit 124 gives the console 28, the display device 26, etc. a warning indicating that the image capturing apparatus 22 and the cassette holder 206 are not placed in the desired position.

Accordingly, the cassette holder 206 and the image capturing apparatus 22 can be placed in head-on facing relation to each other before the radiation detecting cassette 24 is set on the cassette holder 206. Therefore, it is possible to confirm quickly whether the image capturing apparatus 22 is positioned laterally of the cassette holder 206 in horizontally head-on facing relation thereto irrespectively of whether the radiation detecting cassette 24 is set on the cassette holder 206.

The radiation detecting cassette 24 may be set on the cassette holder 206 before the image capturing apparatus 22 and the cassette holder 206 are brought into head-on facing relation to each other. If the radiation detecting cassette 24 are set on the cassette holder 206 before the image capturing apparatus 22 and the cassette holder 206 are brought into head-on facing relation to each other, then it is determined whether or not the image capturing apparatus 22, the radiation detecting cassette 24, and the cassette holder 206 are positioned in horizontally head-on facing relation to each other based on the radio waves emitted from the first, second, and third transceivers 29a, 29b, 29c.

When the radiation detecting cassette 24 is used in the operating room 12 or the like, the radiation detecting cassette 24 may be subjected to adhesion of blood, contamination, etc. However, when the radiation detecting cassette 24 is designed to have a waterproof and hermetically-sealed structure, and is sterilized and cleaned as necessary, one radiation detecting cassette 24 can be used repeatedly.

The radiation detecting cassette 24 is not limited to use in the operating room 12, and may be used for a medical examination and a round in the hospital.

Also, the radiation detecting cassette 24 may communicate with external devices via optical wireless communication using infrared light or the like, instead of general wireless communication using radio wave.

Figure 12:
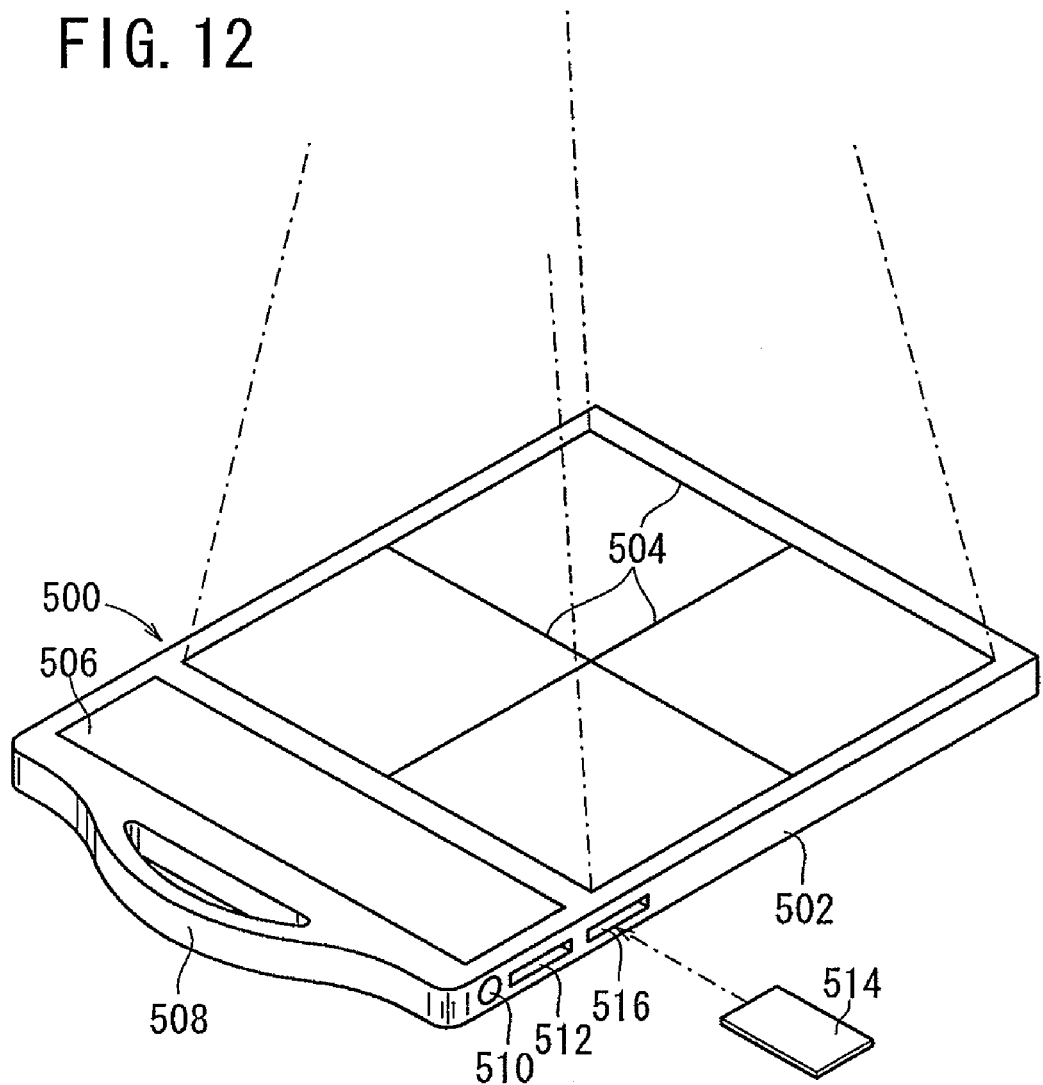
FIG. 12 is a perspective view showing a radiation detecting cassette according to further still another embodiment of the present invention.

Preferably, the radiation detecting cassette 500 may be constructed as shown in FIG. 12.

Specifically, the radiation detecting cassette 500 includes a guiding line 504 drawn on the radiation-irradiated surface of a casing 502, the guiding line 504 serving as a reference for setting a captured area and a captured position. Using the guiding line 504, a subject can be positioned with respect to the radiation detecting cassette 500, and an area irradiated with the radiation can be set, thereby recording radiation image information on an appropriate captured area.

The radiation detecting cassette 500 is provided with a display section 506 on an area thereof other than the captured area, for displaying various information about the radiation detecting cassette 500. The information which is displayed on the display section 506, includes ID information of a subject whose radiation image information is to be recorded on the radiation detecting cassette 500, the number of times the radiation detecting cassette 500 has been used, an accumulated exposed radiation dose, a charging state (remaining battery level) of a battery 44 in the radiation detecting cassette 500, image capturing conditions of radiation image information, and a positioning image of the subject with respect to the radiation detecting cassette 500. In this case, a technician confirms a subject based on the ID information displayed on the display section 506, for example, and also previously confirms that the radiation detecting cassette 500 is placed in a usable state. Then, the technician positions a desired captured area of the subject with respect to the radiation detecting cassette 500 based on the displayed positioning image, thereby capturing appropriate radiation image information.

Also, the radiation detecting cassette 500 is provided with a handgrip 508, whereby it is easier to handle and carry the radiation detecting cassette 500.

Preferably, the radiation detecting cassette 500 may have, on a side thereof, an input terminal 510 for an AC adapter, a USB (Universal Serial Bus) terminal 512, and a card slot 516 for inserting a memory card 514.

When the charging function of the battery 44 in the radiation detecting cassette 500 becomes deteriorated, or when there is not enough time to fully charge the battery 44, the input terminal 510 is connected to the AC adapter to externally supply the radiation detecting cassette 500 with electric power, thereby enabling the radiation detecting cassette 500 to be used immediately.

The USB terminal 512 or the card slot 516 may be used when the radiation detecting cassette 500 cannot transmit and receive information to and from external devices such as the console 28 via wireless communication. Specifically, by connecting a cable to the USB terminal 512, the radiation detecting cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 13:
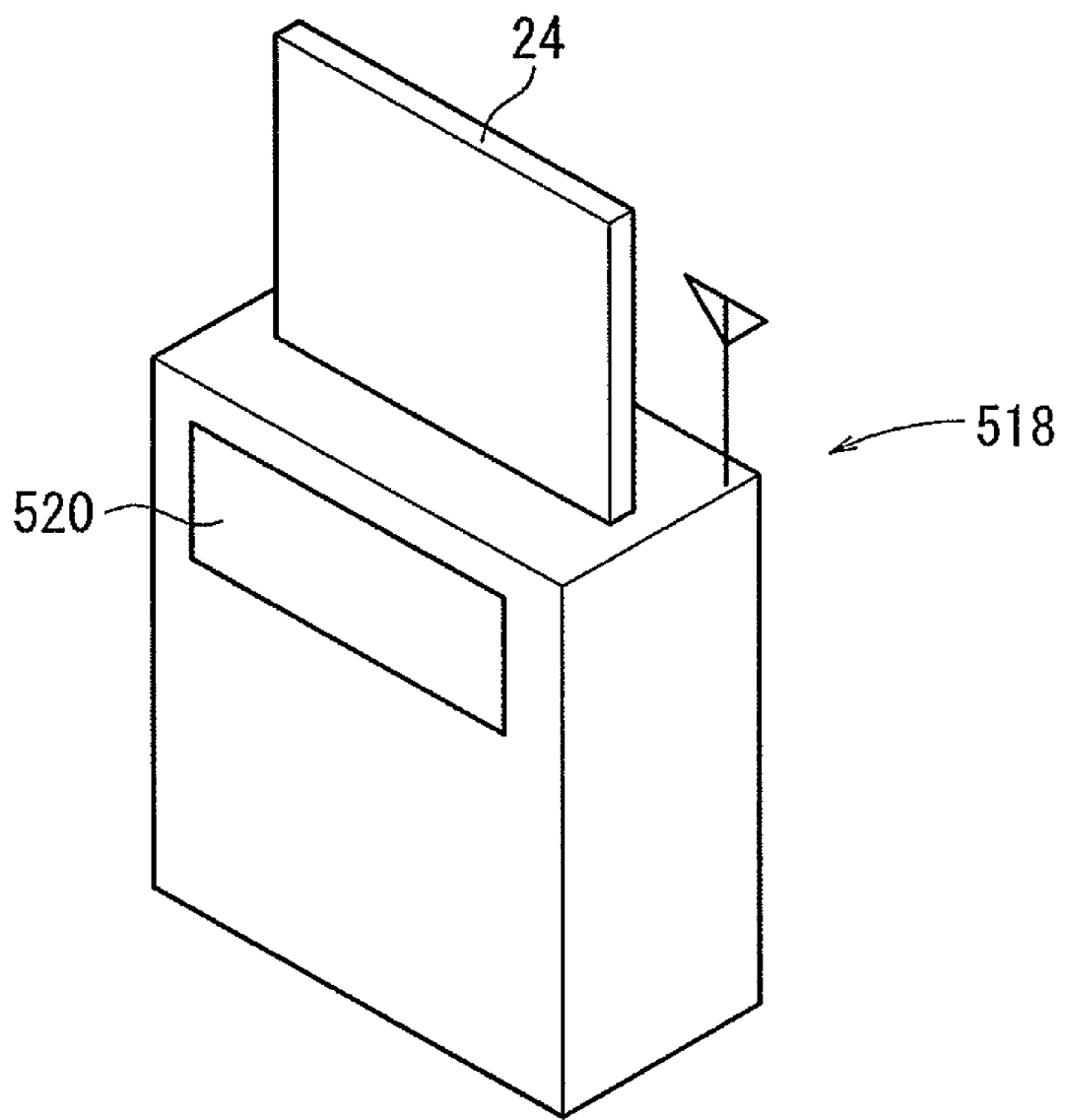
FIG. 13 is a perspective view showing a cradle which charges the radiation detecting cassette.

Preferably, a cradle 518 may be disposed in the operating room 12 or at a desired place in the hospital, into which the radiation detecting cassette 24 is inserted to charge the internal battery 44, as shown in FIG. 13. In this case, in addition to charging the battery 44, the cradle 518 may transmit and receive necessary information to and from external devices such as HIS, RIS, the console 28, etc. by way of wireless or wire communications of the cradle 518. The information may include radiation image information which is recorded on the radiation detecting cassette 24 inserted into the cradle 518.

Also, the cradle 518 may be provided with a display section 520. The display section 520 may display necessary information including a charging state of the inserted radiation detecting cassette 24 and radiation image information acquired from the radiation detecting cassette 24.

Further, a plurality of cradles 518 may be connected to a network. In this case, information about charging states of radiation detecting cassettes 24 inserted in respective cradles 518 can be collected through the network, and the radiation detecting cassette 24 in a usable state can be located.

Although certain preferred embodiments of the present invention have been shown and described in detail, it should be understood that various changes and modifications may be made therein without departing from the scope of the appended claims.

What is claimed is:

1. A radiation image capturing system comprising:
   an image capturing unit including a radiation source for emitting a radiation;
   a cassette including a radiation conversion panel for detecting the radiation which has been emitted from said radiation source and which has passed through a subject, and converting the detected radiation into radiation image information;
   a position detecting unit for detecting respective positions of said radiation source and said radiation conversion panel; and
   a determining unit for determining whether said radiation source and said radiation conversion panel are placed in head-on facing relation to each other based on the positions of said radiation source and said radiation conversion panel which are detected by said position detecting unit;
   wherein said radiation source and said radiation conversion panel are separate from each other and movable with respect to each other.

2. A radiation image capturing system according to claim 1, wherein said position detecting unit is mounted on said image capturing unit, said cassette, and a cassette holder for holding said cassette.

3. A radiation image capturing system according to claim 2, wherein said position detecting unit comprises a detector for detecting the respective positions of said radiation source and said radiation conversion panel in a horizontal plane.

4. A radiation image capturing system according to claim 3, wherein said image capturing unit includes an actuating unit for moving said image capturing unit to a position which faces said radiation conversion panel head-on, and said actuating unit is energizable based on a determined result from said determining unit.

5. A radiation image capturing system according to claim 4, further comprising a warning unit for issuing a warning if said determining unit judges that said radiation source and said radiation conversion panel are not placed in head-on facing relation to each other based on the determined result from said determining unit.

6. A radiation image capturing system according to claim 4, wherein said detector comprises an azimuthal sensor for detecting a spatial position, a gravitational sensor, or an acceleration sensor for detecting an acceleration upon displacement of said cassette.

* * * * *